United States Patent
Joo et al.

(10) Patent No.: US 8,124,238 B2
(45) Date of Patent: Feb. 28, 2012

(54) DENDRIMER HAVING METALLOCENE CORE, ORGANIC MEMORY DEVICE USING THE SAME AND MANUFACTURING METHOD THEREOF

(75) Inventors: Won Jae Joo, Seongnam-si (KR); Chulhee Kim, Seongnam-si (KR); Kwang Hee Lee, Suwon-si (KR); Tae Lim Choi, Suwon-si (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 1076 days.

(21) Appl. No.: 11/898,979

(22) Filed: Sep. 18, 2007

(65) Prior Publication Data
US 2008/0241559 A1    Oct. 2, 2008

(30) Foreign Application Priority Data
Apr. 2, 2007  (KR) .................. 10-2007-0032325

(51) Int. Cl.
B32B 15/04  (2006.01)
B32B 15/20  (2006.01)
B05D 1/00  (2006.01)
B05D 1/02  (2006.01)
B05D 1/04  (2006.01)
B05D 1/18  (2006.01)

(52) U.S. Cl. ........ 428/447; 428/457; 428/469; 428/472; 428/704; 427/58; 427/427.4; 427/427.5; 427/428.1; 427/430.1; 427/435; 427/458; 257/40; 438/99

(58) Field of Classification Search .................. None
See application file for complete search history.

(56) References Cited

U.S. PATENT DOCUMENTS

| 7,045,367 B2* | 5/2006 | Kaganove et al. ............ 436/532 |
| 7,537,842 B2* | 5/2009 | Burn et al. .................... 428/690 |
| 2002/0163057 A1 | 11/2002 | Bulovic et al. | |
| 2004/0027849 A1 | 2/2004 | Yang et al. | |

FOREIGN PATENT DOCUMENTS

JP   62-095882   5/1987
WO   WO 2005092906 A1 * 10/2005

OTHER PUBLICATIONS

Astruc, Organometallic chemistry at the nanoscale. Dendrimers for redox processes and catalysis, 2003, Pure Appl. Chem., vol. 75, No. 4, pp. 461-481.*

(Continued)

Primary Examiner — Monique Jackson
(74) Attorney, Agent, or Firm — Harness, Dickey & Pierce, P.L.C.

(57) ABSTRACT

Disclosed herein is a dendrimer, in which metallocene, which is an oxidation-reduction material, is located at a core, and a conjugated dendron is connected to the metallocene core by a linker compound, an organic active layer having the dendrimer, an organic memory device having the organic active layer and a method of manufacturing the organic active layer and the organic memory device. The organic memory device manufactured using a dendrimer having a metallocene core of example embodiments may have a shorter switching time, decreased operation voltage, decreased manufacturing cost and increased reliability, thereby realizing a highly-integrated large-capacity memory device.

16 Claims, 6 Drawing Sheets

OTHER PUBLICATIONS

Cardona et al, Asymmetric Redox-Active Dendrimers Containing a Ferrocene Subunit. Preparation, Characterization and Electrochemistry, 1998, J. Am. Chem. Soc., 120, pp. 4023-4024.*

Muller et al, Results and perspectives in the chemistry of side-chain-functionalized cyclopentadienyl compounds, 200, Journal of Organometalllic Chemistry, 600, pp. 127-143.*

Chase et al, Where organometallics and dendrimers merge: the incorporation of organometallic species into dentritic molecules, 2004, Journal of Organometallic Chemistry, 689, pp. 4016-4054.*

Kaifer, Electron Transfer and Molecular Recognition in Metallocene-Containing Dendrimers, Aug. 17, 2007, Eur. J. Inorg. Chem., pp. 5015-5027.*

* cited by examiner

DENDRIMER HAVING METALLOCENE CORE, ORGANIC MEMORY DEVICE USING THE SAME AND MANUFACTURING METHOD THEREOF

PRIORITY STATEMENT

This application claims priority under U.S.C. §119 to Korean Patent Application No. 10-2007-0032325, filed on Apr. 2, 2007, in the Korean Intellectual Property Office (KIPO), the entire contents of which are incorporated herein by reference.

BACKGROUND

1. Field

Example embodiments relate to a dendrimer, an organic active layer having the dendrimer, an organic memory device having the organic active layer and methods of manufacturing the organic active layer and the organic memory device. Other example embodiments relate to a dendrimer, in which metallocene, which is an oxidation-reduction material, may be located at a core, and a conjugated dendron may be connected to the metallocene core by a linker compound, an organic active layer having the dendrimer, an organic memory device having the organic active layer, having improved operating characteristics and nonvolatility, manufactured using the dendrimer, and methods of manufacturing the organic active layer and the organic memory device.

2. Description of the Related Art

As information and communication industries have grown, the demands for various memory devices are increasing. For example, the use of portable computers or electronic apparatuses, e.g., portable terminals, various smart cards, electronic cashes, personal digital assistants, digital audio players and/or multi-media players, is increased, and thus the memory devices necessary for these apparatuses may be nonvolatile memory devices in which recorded information is not erased even when no power is being applied to the memory device.

Memory devices may include bistable elements which may be switched between a higher resistive state and a lower resistive state when voltage is applied to the memory devices. Resistive memory devices are memory devices in which resistance is varied depending on voltage and data is stored depending on the variation of resistances.

Chalcogenide materials, semiconductors, various oxides and nitrides may have these resistive memory properties. Organic materials may also have the resistive memory properties. Such organic memory devices may realize memory properties using the bistability of resistance values obtained by forming a memory layer between the upper and lower electrodes using organic materials and applying voltage to the memory layer. These organic memory devices are expected to be next-generation memory because they may overcome problems in processability, manufacturing cost, and integration degree, which are disadvantages of conventional flash memory, while realizing nonvolatility, which is an advantage of conventional flash memory.

As examples of organic memory devices, an organic memory device may be manufactured using a complex of copper and TCNQ (7,7,8,8-tetracyano-p-quinodimethane), which is a charge transfer compound of organic metal complex. In another example, a semiconductor device including an intermediate layer, in which an ionic salt, e.g., NaCl and/or CsCl, may be mixed with a conductive polymer, between the upper and lower electrodes.

Finally, an organic memory device may apply metal nanoclusters between organic active layers. However, this organic memory device may have a problem in that it may not be practically used as a nonvolatile organic memory because the yield may be lower, methods of forming metal nanoclusters may not be easily performed, and a phenomenon in which the device is reset at 0V voltage may occur.

Research on metallocene and derivatives thereof has been conducted because metallocene and derivatives thereof have unique electrochemical, optical and magnetic properties, for example, metallocenes may form a mixed valence state by oxidation. However, the research on the use of metallocene has only been as a fuel additive or a polymerizing catalyst.

SUMMARY

Accordingly, example embodiments may have been made to overcome the above problems occurring in the related art, and example embodiments provide a dendrimer having a metallocene core as a material, which may improve operating characteristics when the dendrimer is used as a material for an organic active layer of an organic memory device. Other example embodiments provide an organic active layer including the dendrimer.

Example embodiments also provide an organic memory device including the organic active layer having a metallocene core, which has a shorter switching time, decreased operating voltage, decreased manufacturing cost, and increased reliability.

Example embodiments provide methods of manufacturing the organic active layer and the organic memory device, in which the manufacturing cost may be reduced, the manufacturing process may be simplified, and relatively low temperature processing may be performed.

Example embodiments provide a dendrimer having a metallocene core, in which metallocene is located at a core, and a conjugated dendron is connected to the core using one selected from the group consisting of an ester group of about 1 to about 20 carbon atoms, a ketone group of about 1 to about 20 carbon atoms, an alkylene group of about 1 to about 20 carbon atoms, and an amide group of about 1 to about 20 carbon atoms as a linker.

For example, the dendrimer having a metallocene core according to example embodiments may be represented by Formula 1 below:

[Formula 1]

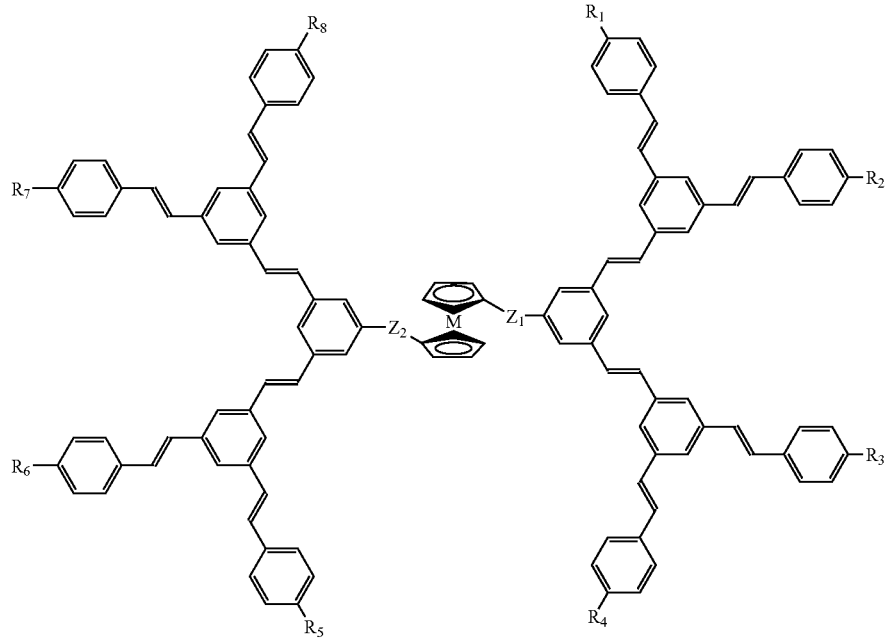

wherein, $R_1, R_2, R_3, R_4, R_5, R_6, R_7$ and $R_8$ are identical to or different from each other, and each of them is one or more independently selected from the group consisting of substituted or unsubstituted stilbene, acetylene, vinylene phenylene, fluorene, phenylene ethynylene, naphthalene, anthracene, tetracene, perylene, pyrene, thiophene, pyridine vinylene, aniline, and triphenylamine, substituted groups are identical to or different form each other, and each of them is independently selected from the group consisting of an alkyl group of $C_1$-$C_{20}$, a cycloalkyl group of $C_3$-$C_{20}$, a heterocycloalkyl group of $C_5$-$C_{30}$, an alkenyl group of $C_2$-$C_{20}$, an aryl group of $C_6$-$C_{20}$, a heteroaryl group of $C_5$-$C_{30}$, an arylalkyl group of $C_7$-$C_{20}$, and a heteroarylalkyl group of $C_7$-$C_{30}$, $Z_1$ and $Z_2$ are identical to or different from each other, and each of them is independently selected from the group of consisting of an ester group of about 1 to about 20 carbon atoms, a ketone group of about 1 to about 20 carbon atoms, an alkylene group of about 1 to about 20 carbon atoms, and an amide group of about 1 to about 20 carbon atoms, and M is Fe, Ru, Zr or Ti.

For example, the dendrimer having a metallocene core according to example embodiments, represented by the above Formula 1, may be represented by Formulas 2 to 4 below.

[Formula 2]

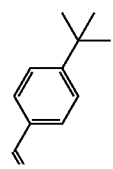
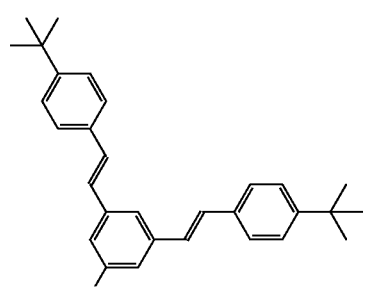

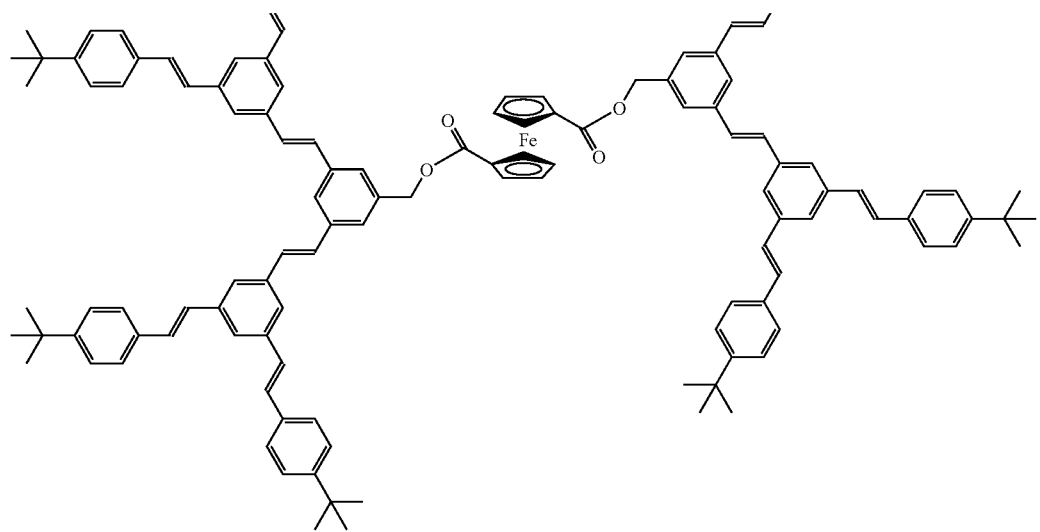
[Formula 3]
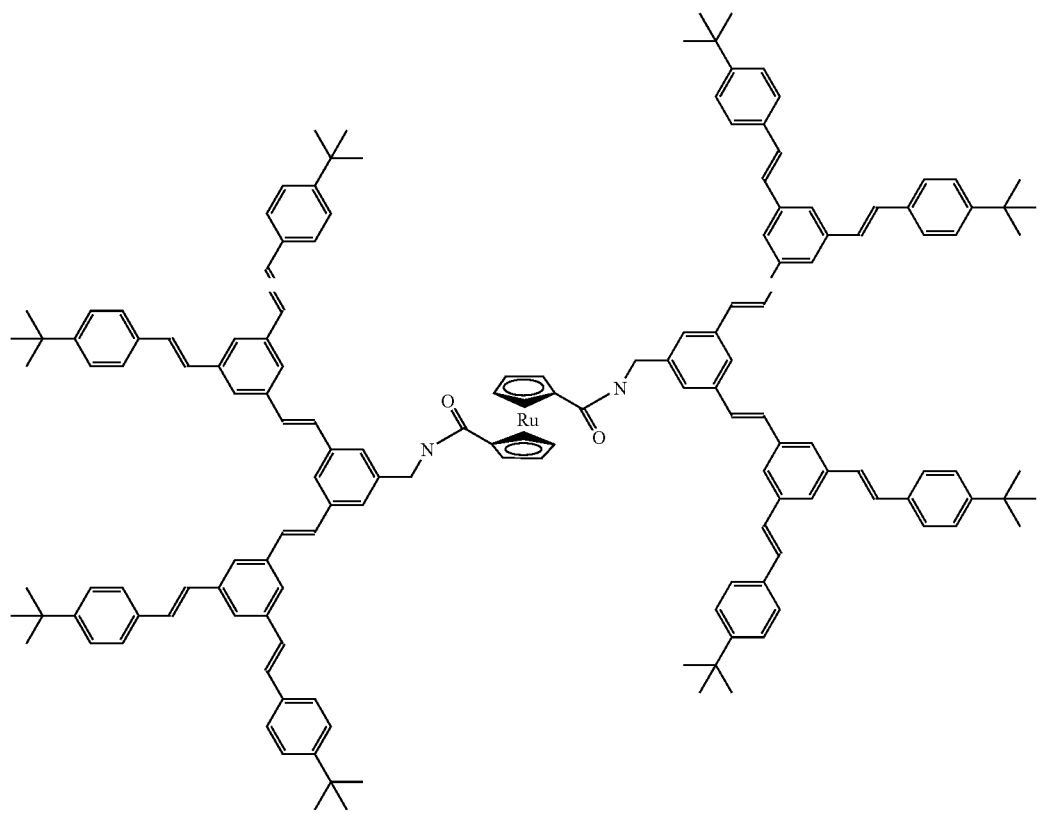

-continued

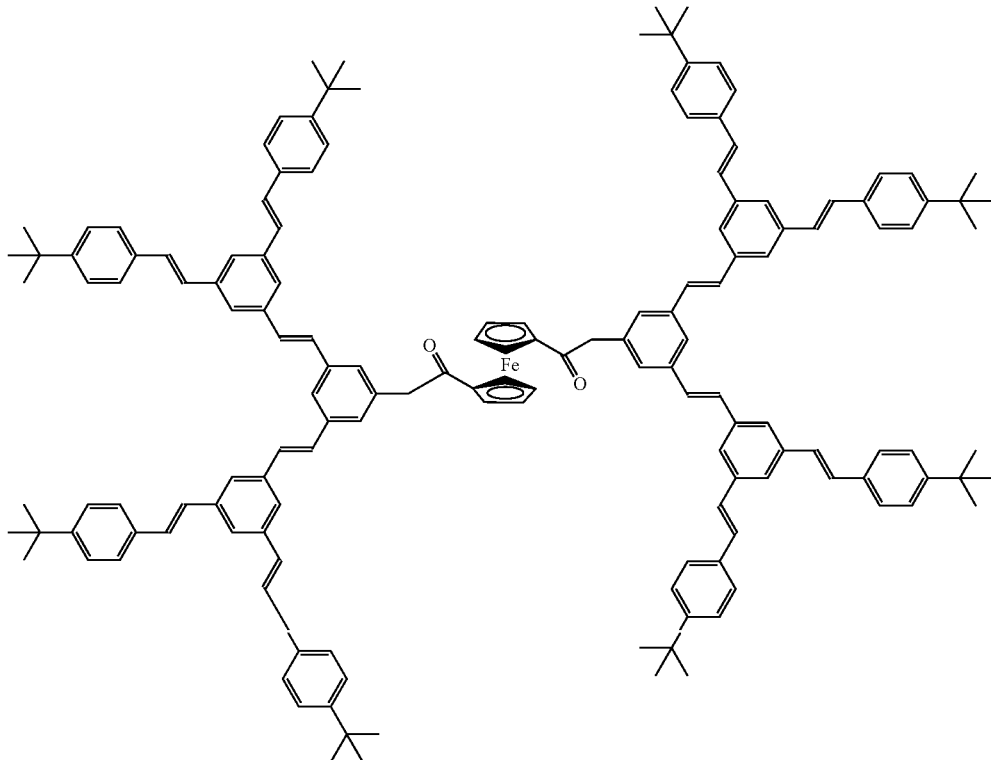

[Formula 4]

Example embodiments provide an organic active layer including the dendrimer having a metallocene core, in which metallocene is located at a core, and a conjugated dendron is connected to the core using one selected from the group consisting of an ester group of about 1 to about 20 carbon atoms, a ketone group of about 1 to about 20 carbon atoms, an alkylene group of about 1 to about 20 carbon atoms, and an amide group of about 1 to about 20 carbon atoms as a linker. Example embodiments also provide an organic memory device, including the organic active layer formed between a first electrode and a second electrode.

Other example embodiments provide methods of manufacturing an active layer and an organic memory device, in which the memory device may include the organic active layer formed between a first electrode and a second electrode. The organic active layer may be formed using the dendrimer having a metallocene core, in which metallocene is located at a core, and a conjugated dendron is connected to the core using one selected from the group consisting of an ester group of about 1 to about 20 carbon atoms, a ketone group of about 1 to about 20 carbon atoms, an alkylene group of about 1 to about 20 carbon atoms, and an amide group of about 1 to about 20 carbon atoms as a linker.

BRIEF DESCRIPTION OF THE DRAWINGS

Example embodiments will be more clearly understood from the following detailed description taken in conjunction with the accompanying drawings.

FIG. 1 is a schematic sectional view illustrating an organic memory device according to example embodiments;

FIG. 2 is a schematic perspective view illustrating a memory matrix fabricated using the organic memory device according to example embodiments;

FIGS. 3, 4, and 5 are graphs illustrating the results of analyzing the dendrimer having a metallocene core obtained in Preparation Example 1 through $^1$H-NMR, $^{13}$C-NMR and MALDI-TOF, respectively;

FIG. 6 is a graph illustrating the absorbance and photoluminescence (PL) intensity of the dendrimer having a metallocene core obtained in Preparation Example 1;

FIG. 7 is a graph illustrating the variation of current depending on the voltage applied to the organic memory device manufactured in Example 1 according to example embodiments; and FIG. 8 is a graph illustrating the variation of resistance depending on the voltage applied to the organic memory device manufactured in Example 1 according to example embodiments.

Figure 1:
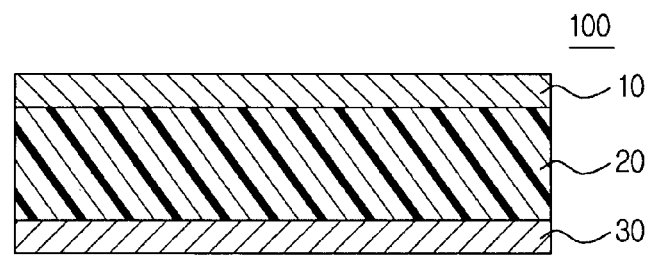
FIGS. 1-8 represent non-limiting, example embodiments as described herein.

It should be noted that these Figures are intended to illustrate the general characteristics of methods, structure and/or materials utilized in certain example embodiments and to supplement the written description provided below. These drawings are not, however, to scale and may not precisely reflect the precise structural or performance characteristics of any given embodiment, and should not be interpreted as defining or limiting the range of values or properties encompassed by example embodiments. For example, the relative thicknesses and positioning of molecules, layers, regions and/or structural elements may be reduced or exaggerated for clarity. The use of similar or identical reference numbers in the various drawings is intended to indicate the presence of a similar or identical element or feature.

DETAILED DESCRIPTION OF EXAMPLE EMBODIMENTS

Hereinafter, example embodiments will be described in detail with reference to the attached drawings. Reference now should be made to the drawings, in which the same reference numerals are used throughout the different drawings to designate the same or similar components. In the drawings, the thicknesses and widths of layers are exaggerated for clarity. Example embodiments may, however, be embodied in many different forms and should not be construed as limited to the example embodiments set forth herein. Rather, these example embodiments are provided so that this disclosure will be thorough and complete, and will fully convey the scope of example embodiments to those skilled in the art.

It will be understood that when an element or layer is referred to as being "on", "connected to" or "coupled to" another element or layer, it can be directly on, connected or coupled to the other element or layer or intervening elements or layers may be present. In contrast, when an element is referred to as being "directly on," "directly connected to" or "directly coupled to" another element or layer, there are no intervening elements or layers present. Like numbers refer to like elements throughout. As used herein, the term "and/or" includes any and all combinations of one or more of the associated listed items.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of example embodiments.

Spatially relative terms, such as "beneath," "below," "lower," "above," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly.

The terminology used herein is for the purpose of describing particular embodiments only and is not intended to be limiting of example embodiments. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Example embodiments are described herein with reference to cross-sectional illustrations that are schematic illustrations of idealized embodiments (and intermediate structures) of example embodiments. As such, variations from the shapes of the illustrations as a result, for example, of manufacturing techniques and/or tolerances, are to be expected. Thus, example embodiments should not be construed as limited to the particular shapes of regions illustrated herein but are to include deviations in shapes that result, for example, from manufacturing. For example, an implanted region illustrated as a rectangle will, typically, have rounded or curved features and/or a gradient of implant concentration at its edges rather than a binary change from implanted to non-implanted region. Likewise, a buried region formed by implantation may result in some implantation in the region between the buried region and the surface through which the implantation takes place. Thus, the regions illustrated in the figures are schematic in nature and their shapes are not intended to illustrate the actual shape of a region of a device and are not intended to limit the scope of example embodiments.

Unless otherwise defined, all terms (including technical and scientific terms) used herein have the same meaning as commonly understood by one of ordinary skill in the art to which example embodiments belong. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

In example embodiments, the term "dendrimer" refers to a material having a regularly repeated dendritic or radial branched structure. Dendrimer becomes a spherical molecule by forming radial chains around a central core molecule. The branches of the dendrimer may grow by steps while forming a layer, with each step referred to as "generation".

Example embodiments provide a dendrimer having a metallocene core, in which metallocene may be located at a core, and a conjugated dendron may be connected to the core using one selected from the group consisting of an ester group of about 1 to about 20 carbon atoms, a ketone group of about 1 to about 20 carbon atoms, an alkylene group of about 1 to about 20 carbon atoms, and an amide group of about 1 to about 20 carbon atoms as a linker.

The dendrimer having a metallocene core of example embodiments may be a relatively low molecular material in which metallocene, which may have about two or more oxidation states, may be located at a core, and a conjugated dendron may be linked to the core using a linker, and may realize bistable memory characteristics due to the reversible oxidation-reduction reaction of a metallocene group. Because this dendrimer having a metallocene core is a low-molecular and soluble material, an organic active layer of an organic memory device may be formed using this dendrimer in a solution process, e.g., a spin coating process. The molecular weight of the metallocene dendrimer may be in the range of about 1000 to about 10000.

The linker connecting a conjugated dendron with metallocene may serve as a barrier for preventing or reducing the charges transferred through the conjugation of the metallocene and dendron in the dendrimer molecule from returning to an original state, thereby maintaining the state in which charges were transferred.

In the dendrimer having a metallocene core of example embodiments, the metallocene may be selected from the group consisting of ferrocene, ruthenocene, zirconocene and/or titanocene, and the conjugated dendron may be one or a combination thereof selected from the group consisting of stilbene, acetylene, vinylene phenylene, fluorene, phenylene ethynylene, naphthalene, anthracene, tetracene, perylene, pyrene, thiophene, pyridine vinylene, aniline and/or triphenylamine.

In the dendrimer having a metallocene core of example embodiments, the conjugated dendron may have one or more substituted groups. These substituted groups may be identical to or different from each other, and, for example, may include, but are not limited to, an alkyl group of $C_1$-$C_{20}$, a cycloalkyl group of $C_3$-$C_{20}$, a heterocycloalkyl group of $C_5$-$C_{30}$, an alkenyl group of $C_2$-$C_{20}$, an aryl group of $C_6$-$C_{20}$, a heteroaryl group of $C_5$-$C_{30}$, an arylalkyl group of $C_7$-$C_{20}$ and/or a heteroarylalkyl group of $C_7$-$C_{30}$.

In example embodiments, the alkyl group may include a methyl group, an ethyl group, a propyl group, an isobutyl group, a sec-butyl group, a tert-butyl group, a pentyl group, an iso-amyl group and/or a hexyl group, which are straight-chained or branched groups.

In example embodiments, the cycloalkyl group refers to a monovalent monocyclic system of about 3 to about 20 carbon atoms. One or more hydrogen atoms of the cycloalkyl group may be substituted. The heterocycloalkyl group refers to a monovalent monocyclic system of about 5 to about 30 ring atoms, which may include one, two, or three hetero ring atoms selected from among N, O, P, and S, and in which residual ring atoms are Cs. One or more hydrogen atoms of the heterocycloalkyl group may be substituted.

For example, the alkenyl group may include a vinyl group, an allyl group, a propenyl group, a butenyl group, a hexenyl group and/or a cyclohexenyl group. The aryl group refers to a carbocyclic aromatic system having one or more aromatic rings, and the aromatic rings may be bonded and fused together through a pendent method. For example, the aryl group may include aromatic groups e.g., a phenyl group, a naphthyl group and/or a tetrahydronaphthyl group. One or more hydrogen atoms of the aryl group may be substituted.

The heteroaryl group refers to a cyclic aromatic system of about 5 to about 30 ring atoms, which may include one, two, or three hetero ring atoms selected from among N, O, P, and S, and in which residual ring atoms are Cs, and the rings may be bonded and fused together through a pendent method. One or more hydrogen atoms of the heteroaryl group may be substituted.

The arylalkyl group refers to a group in which some hydrogen atoms of the aryl group mentioned above are substituted with lower alkyls, for example, radicals, e.g., methyl, ethyl and/or propyl. The arylalkyl group may include a benzyl group and/or a phenylethyl group. One or more hydrogen atoms of the arylalkyl group may be substituted.

The heteroarylalkyl group refers to a group in which some hydrogen atoms of the heteroaryl group mentioned above are substituted with lower alkyls. In the heteroarylalkyl group, the heteroaryl group was described as above. One or more hydrogen atoms of the heteroarylalkyl group may be substituted with the substituted groups the same as in the alkyl group.

For example, the dendrimer having a metallocene core according to example embodiments may be represented by Formula 1 below:

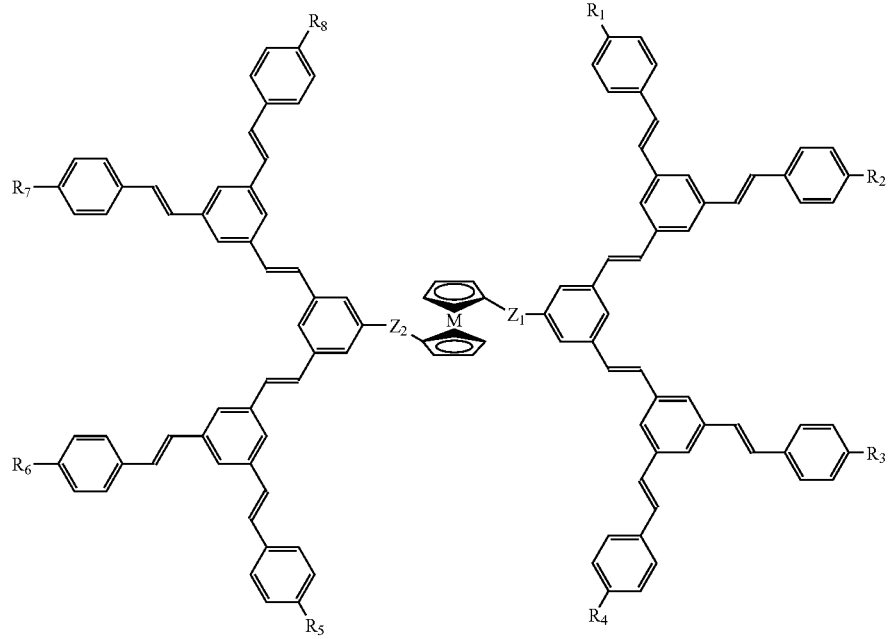

[Formula 1]

wherein, $R_1$, $R_2$, $R_3$, $R_4$, $R_5$, $R_6$ $R_7$ and $R_8$ are identical to or different from each other, and each of them is one or more independently selected from the group consisting of substituted or unsubstituted stilbene, acetylene, vinylene phenylene, fluorene, phenylene ethynylene, naphthalene, anthracene, tetracene, perylene, pyrene, thiophene, pyridine vinylene, aniline, and triphenylamine, substituted groups are identical to or different from each other, and each of them is independently selected from the group consisting of an alkyl group of $C_1$-$C_{20}$, a cycloalkyl group of $C_3$-$C_{20}$, a heterocycloalkyl group of $C_5$-$C_{30}$, an alkenyl group of $C_2$-$C_{20}$, an aryl group of $C_6$-$C_{20}$, a heteroaryl group of $C_5$-$C_{30}$, an arylalkyl group of $C_7$-$C_{20}$, and a heteroarylalkyl group of $C_7$-$C_{30}$, $Z_1$ and $Z_2$ are identical to or different from each other, and each of them is independently selected from the group of consisting of an ester group of about 1 to about 20 carbon atoms, a ketone group of about 1 to about 20 carbon atoms, an alkylene group of about 1 to about 20 carbon atoms, and an amide group of about 1 to about 20 carbon atoms, and M is Fe, Ru, Zr or Ti.

For example, the dendrimer having a metallocene core according to example embodiments, represented by the above Formula 1, may be represented by Formulas 2 to 4 below.

[Formula 2]
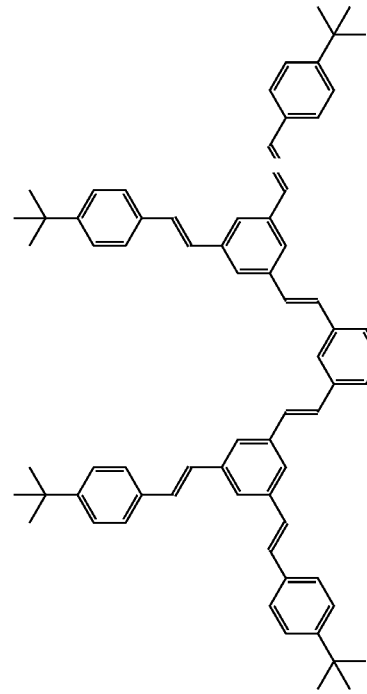
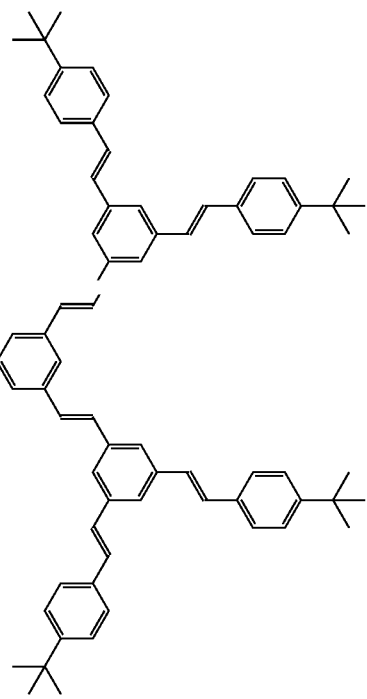
[Formula 3]
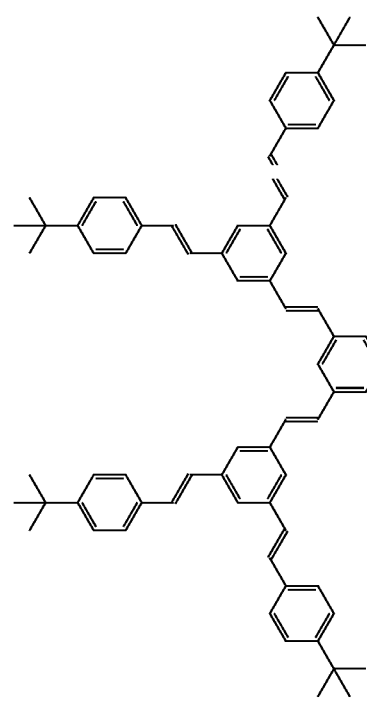
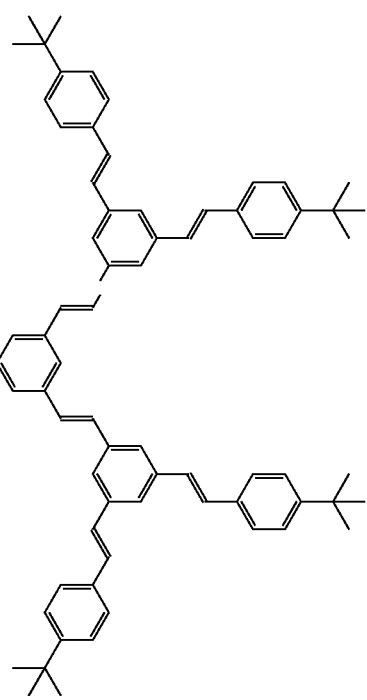

-continued

[Formula 4]

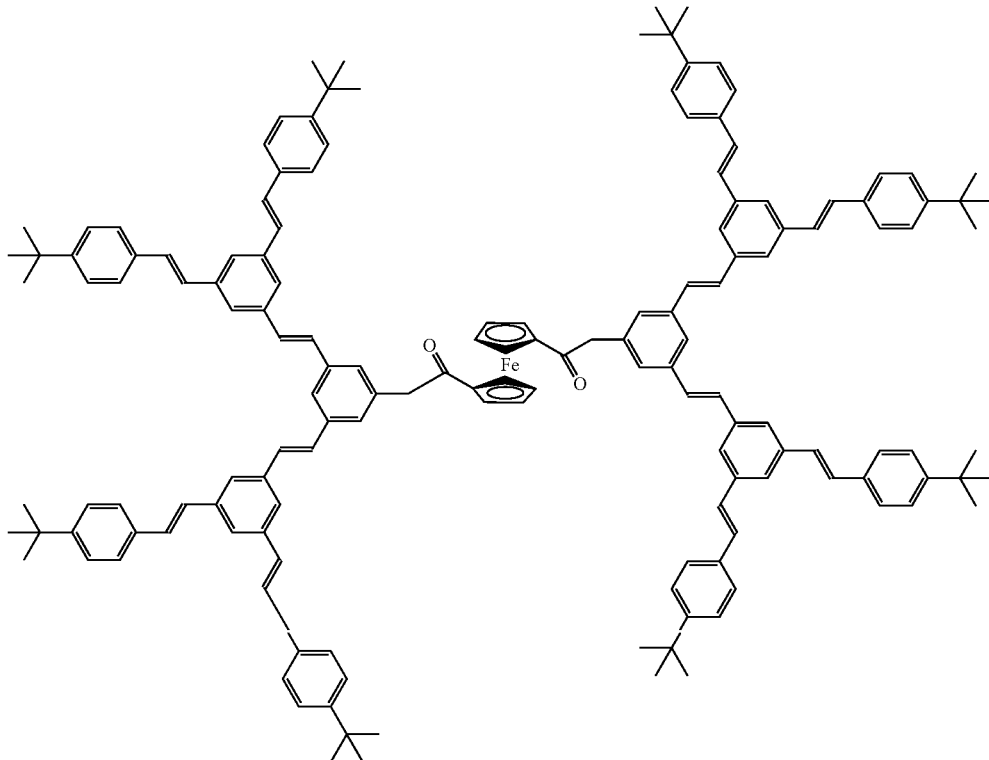

Dendrimer, unlike polymer, may be synthesized to have a predetermined or given accurate molecular weight and structure, and the material properties thereof after synthesis may be predicted. Generally, in a process of synthesizing a polymer, a macromolecule may be formed through the partial decomposition and cross-linking of functional groups. In contrast, in a process of synthesizing a dendrimer, the dendrimer may be synthesized using a multi-step synthesis method in which two or three chemical processes are repeatedly performed, and the synthesized compound may have calculated functional groups on the surface thereof. Various chemical synthesis methods may be used as a method of synthesizing a dendrimer.

Various dendrimers may be synthesized by selecting the types of compounds for forming branch terminals, compounds serving as a monomer for forming dendritic structures, compounds serving as a linker for connecting the dendritic structure with a core, and compounds for forming a core. In the dendrimer having a metallocene core of example embodiments, metallocene may be used as the compound for forming a core, and one or a combination thereof selected from the group consisting of stilbene, acetylene, vinylene phenylene, fluorene, phenylene ethynylene, naphthalene, anthracene, tetracene, perylene, pyrene, thiophene, pyridine vinylene, aniline, and triphenylamine may be used as the compound serving as a monomer for forming dendritic structures. One selected from the group consisting of an ester group of about 1 to about 20 carbon atoms, a ketone group of about 1 to about 20 carbon atoms, an alkylene group of about 1 to about 20 carbon atoms, and an amide group of about 1 to about 20 carbon atoms may be used as the linker. The dendrimer having a metallocene core of example embodiments may be synthesized using a convergence method, a divergence method, or a combination thereof.

The linker for connecting a dendritic structure with a core may serve as a barrier for preventing or reducing the charges transferred through the conjugation of the metallocene and dendron in the dendrimer molecule from returning to an original state, thereby maintaining the state in which charges were transferred.

The dendrimer may be synthesized into a larger molecule using a convergence method or a divergence method. For example, when 3,5-dibromo benzaldehyde is bonded with Stb-vinyl dendron through Heck coupling reaction, the dendrimer is grown by one generation. Further, when the formed aldehyde is converted into a carbon-carbon double bond (C=C) and then reacts with 3,5-dibromo benzaldehyde through a Heck coupling reaction, a larger dendrimer may be synthesized.

Example embodiments provide an organic active layer including the dendrimer having a metallocene core according to example embodiments. Example embodiments provide an organic memory device, including the organic active layer between a first electrode and a second electrode.

FIG. 1 is a schematic sectional view illustrating an organic memory device according to example embodiments. Referring to FIG. 1, the organic memory device 100 of example embodiments may include an organic active layer 20 between a first electrode 10 and a second electrode 30. When voltage is applied to this memory device 100, the resistances of the organic active layer 20 may exhibit bistability, thereby realizing memory characteristics.

The organic active layer 20 of the organic memory device may exhibit conductivity and bistability. The dendrimer having a metallocene core of example embodiments may have electron or hole conductivity due to the conjugation of conjugated molecules. In the dendrimer having a metallocene core of example embodiments, the conductivity thereof may be varied depending on the oxidation-reduction states of metallocene located at a core of the dendrimer, thereby realizing bistability. For example, where voltage is applied to the organic memory device and thus the metallocene, located at the core of the dendrimer included in the organic active layer, obtains or loses one or more electrons, the oxidation state thereof may be changed. The organic active layer formed of dendrimer having a metallocene core may maintain the same oxidation state until different voltage is applied thereto, and this oxidation state may be maintained even when no power is being applied to the memory device. Accordingly, the organic memory device of example embodiments may exhibit improved nonvolatility.

In the synthesized dendrimer according to example embodiments, charges may be transferred in the molecule through the conjugation of metallocene and dendron, and a linker placed between the dendron and metallocene may serve as a barrier for preventing or reducing the transferred charges from returning to an original state, thereby maintaining the state in which charges were transferred. Charges may be transferred between molecules through hopping. For example, ferrocene may exhibit specific conductivity because it is stable in a $Fe^{2+}$ state. However, when a voltage higher than a threshold voltage or light energy having a specific wavelength is applied to the ferrocene, the ferrocene may be excited and may thus be oxidized into $Fe^{3+}$ (Ferrocenium). The charge transfer capacity of ferrocene may be improved, and thus the ferrocene of a $Fe^{3+}$ state may exhibit more improved conductivity than the ferrocene of a $Fe^{2+}$ state. Therefore, in the organic memory device of example embodiments, the oxidation-reduction state of metallocene may act as a factor for determining two resistance states.

Accordingly, when proper voltage is applied between both electrodes of the memory device of example embodiments, the organic active layer may switch between a higher resistance state and a lower resistance state depending on the oxidation-reduction state of metallocene. If the organic active layer of a higher resistance state refers to data "1" and the organic active layer of lower resistance state refers to data "0", data of two logic states may be stored. Accordingly, if the metallocene dendrimer of example embodiments has two or more oxidation states, data of two or more logic states may also be stored.

In addition to the dendrimer having a metallocene core of example embodiments, conductive polymers, e.g., polythiophene, polyvinylcarbazole, polyaniline, polypyrrole, polyphenylenevinylene, polyfluorene and/or polyacetylene, may be used as the material for the organic active layer. For example, this conductive polymer may include poly(9-vinylcarbazole), polyaniline (emeraldine base), poly[2-methoxy-5-(2-ethylhexyloxy)-1,4-phenylenevinylene] and/or poly(9,9-didodecylfluorenyl-2,7-eneethinylene).

Figure 2:
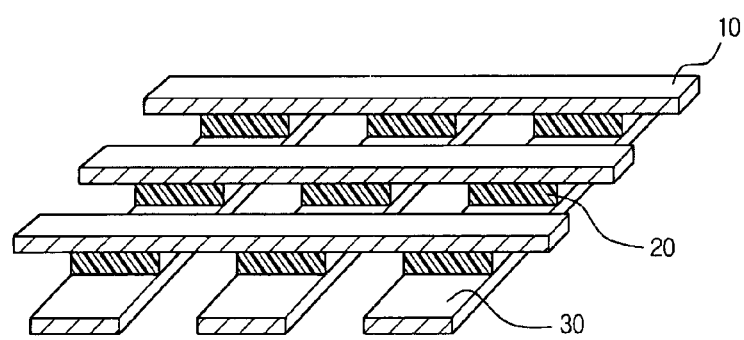

FIG. 2 is a schematic perspective view showing a memory matrix fabricated using the organic memory device according to example embodiments. As shown in FIG. 2, the memory matrix may be formed on a suitable substrate. In this memory matrix, a plurality of memory cells formed on the intersections of first electrodes 10 and second electrodes 30 may exhibit bistability.

In example embodiments, conventional organic or inorganic substrates, e.g., flexible substrates, may be used as the substrate. Further, the substrate may include, but may not be limited to, a glass substrate, a silicon substrate, a surface-reformed glass substrate, a polypropylene substrate, an activated acrylamide ceramic substrate, a membrane substrate, a gel substrate and/or an aerogel substrate.

Each of the first electrode 10 and the second electrode 20 may be formed of one or more conductive materials selected from the group consisting of metals, metal alloys, metal nitrides, metal oxides, metal sulfides, conductive polymers, organic conductors, nanostructures, and crystals. For example, the material for the electrode may include, but may not be limited to, gold (Au), silver (Ag), platinum (Pt), copper (Cu), cobalt (Co), nickel (Ni), tin (Sn), titanium (Ti), tungsten (W), aluminum (Al), and indium tin oxide (ITO).

Specific examples of the conductive polymer may include phenylpolyacetylene polymers, e.g., polydiphenylacetylene, poly(t-butyl)diphenylacetylene, poly(trifluoromethyl)diphenylacetylene, poly(bistrifluoromethyl)acetylene, polybis(t-butyldiphenyl)acetylene, poly(trimethylsilyl)diphenylacetylene, poly(carbazole)diphenylacetylene, polydiacetylene, polyphenylacetylene, polypyridineacetylene, polymethoxyphenylacetylene, polymethylphenylacetylene, poly(t-butyl)phenylacetylene, polynitrophenylacetylene, poly(trifluoromethyl)phenylacetylene, poly(trimethylsilyl)phenylacetylene, and derivatives thereof. Further, other conductive polymers, which may be used in example embodiments, may include polyaniline, polythiophene, polypyrrole, polysilane, polystyrene, polyfuran, polyindole, polyazulene, polyphenylene, polypyridine, polybipyridine, polyphthalocyanine, poly(ethylenedioxythiophene), and derivatives thereof.

In example embodiments, a barrier layer may be additionally formed beneath the first electrode 10 or on the second electrode 30 in order to prevent or reduce damage to the first electrode 10 and second electrode 30 from the organic materials. This barrier layer may include a material selected from the group consisting of SiOx, AlOx, NbOx, TiOx, CrOx, VOx, TaOx, CuOx, MgOx, WOx and AlNOx, and, for example, may include a material selected from the group consisting of $SiO_2$, $Al_2O_3$, $Cu_2O$, $TiO_2$, and $V_2O_3$. Further, the barrier layer of example embodiments may also be formed of an organic material e.g., $Alq_3$, polymethylmethacrylate, polystyrene and/or polyethylene terephthalate (PET). The thickness of the barrier layer may be in the range of about 20 Å to about 300 Å.

The organic memory device of example embodiments may be used in computers, portable information apparatuses, mobile phones, medical instruments, radars and/or satellite equipments, and may be relatively small and light weight. Accordingly, when the organic memory device of example embodiments is used in mobile phones, PDAs, notebook computers, digital cameras, portable multi-media players and/or DMB terminals, portability may be improved.

Example embodiments provide a method of manufacturing an organic active layer using the above mentioned dendrimer having a metallocene core. Example embodiments also provide a method of manufacturing an organic memory device including the organic active layer. When a memory device including an organic active layer between a first electrode and a second electrode is manufactured using the method of example embodiments, the organic active layer may be formed using a dendrimer having a metallocene core. The material for each substrate, electrode and organic active layer may be the same as the organic memory device mentioned above.

In example embodiments, a method of forming an organic active layer using a dendrimer having a metallocene core may include, but may not be particularly limited to, spin coating, spray coating, electrostatic coating, dip coating, blade coating, roll coating and/or ink jet printing. The thickness of the organic active layer may be in the range of about 50 Å to about 3000 Å.

All types of solvents may be used in a spin coating process, as long as they are solvents capable of dissolving a dendrimer having a metallocene core. For example, this solvent may be selected from the group consisting of chloroform, N-methylpyrrolidone, acetone, cyclopentanone, cyclohexanone, methylethylketone, ethyl cellosolve acetate, butylacetate, ethyleneglycol, toluene, xylene, tetrahydrofuran, dimethylformamide, chlorobenzene and/or acetonitrile. The solvent may be used independently or may be used by mixing two or more solvents in a predetermined or given ratio.

Methods of baking the organic active layer, which may be used after the coating of the organic active layer, may differ depending on the kind of solvent used, but the organic active layer may be fired on a hot plate for about 10 minutes or more in consideration of the boiling point of solvent. The first electrode and second electrode may be formed using conventional methods, e.g., thermal deposition, sputtering, e-beam evaporation and/or spin coating.

Hereinafter, example embodiments will be described in detail with reference to Examples. Here, these Examples are set forth to illustrate example embodiments, but should not be construed as the limit of example embodiments.

Preparation Example 1

[Equation 1]

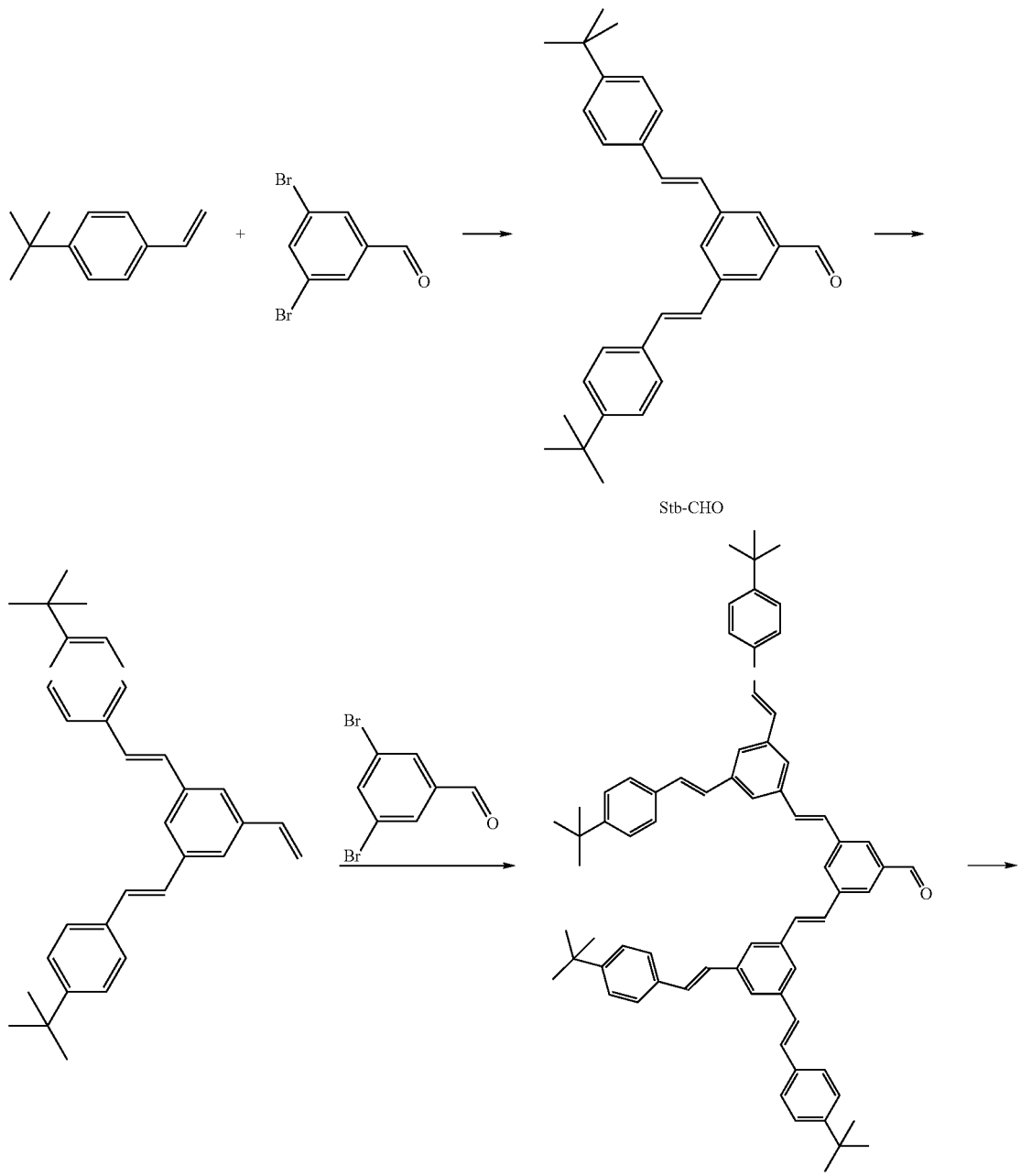

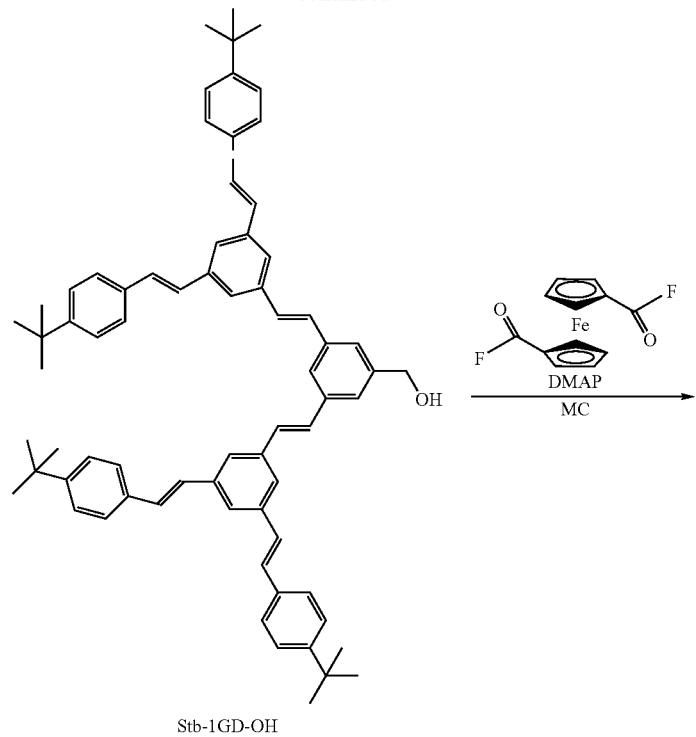
Stb-1GD-OH
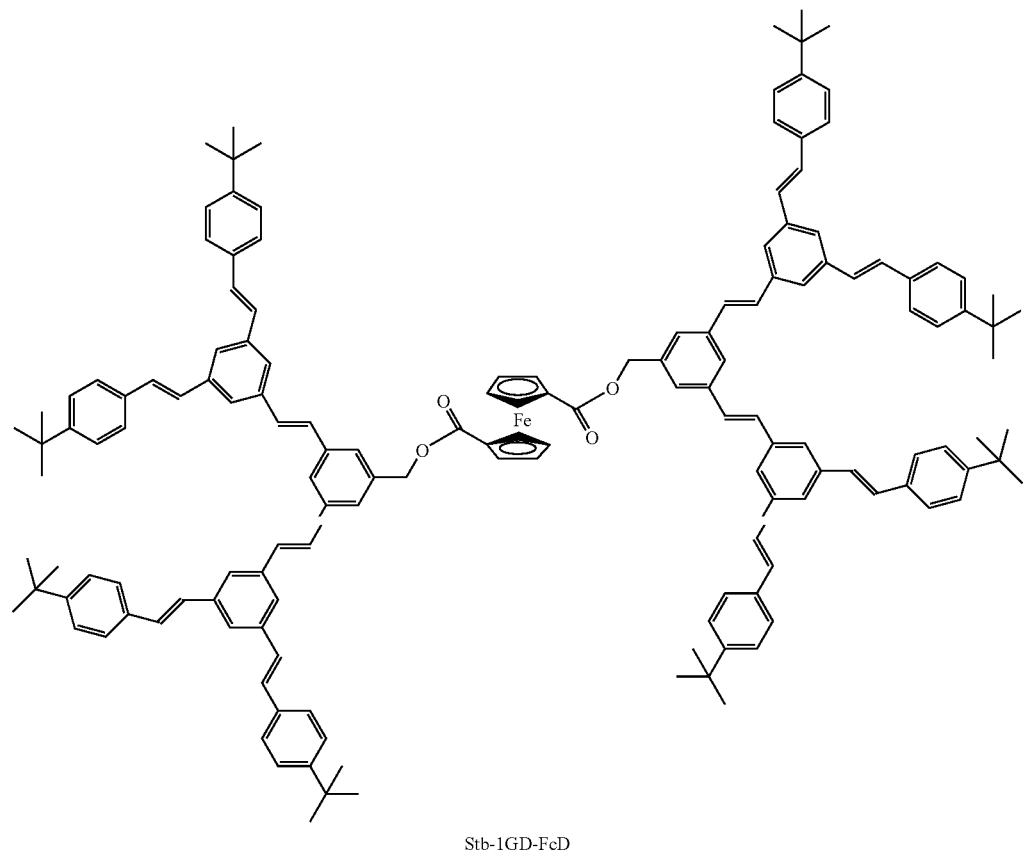
Stb-1GD-FcD

As shown in Equation 1, 3,5-dibromo benzaldehyde and 4-tert-butyl styrene was stirred in dimethylacetamide (DMAC) together with sodium carbonate, 2,6-di-tert-butyl-cresol, and a palladium catalyst at a temperature of about 130° C. for about 48 hours. After the reaction was completed, the reaction mixture was diluted with methylene chloride (MC) and was then washed in water to separate an organic material layer. Then, the separated organic material layer was extracted therefrom, and adsorbed on silica gel. Subsequently, dendron Stb-CHO was separated from the organic material layer adsorbed on silica gel through column chromatography in which a subsidiary solvent having a volume ratio of hexane and methylene chloride of about 2:1 (v/v) may be used as a developing solvent.

Subsequently, in order to grow the synthesized dendron Stb-CHO by a generation, the Stb-CHO was put into a tetrahydrofuran (THF) solution together with methyltriphenylphosphonium iodide and potassium tert-butoxide, and was then stirred at about room temperature for about 3 hours. Subsequently, the reaction mixture was formed into Stb-vinyl dendron through column chromatography. Then, 3,5-dibromo benzaldehyde and the Stb-vinyl dendron was stirred in dimethylacetamide (DMAC) together with sodium carbonate, 2,6-di-tert-butylcresol and a palladium catalyst at a temperature of about 130° C. for about 48 hours. After the reaction was completed, the reaction mixture was diluted with methylene chloride (MC) and was then washed in water to separate an organic material layer. Then, the separated organic material layer was extracted therefrom, and adsorbed on silica gel. Subsequently, STB-1GD-CHO was separated from the organic material layer adsorbed on silica gel through a column chromatography in which a subsidiary solvent having a volume ratio of hexane and methylene chloride of about 2:1 (v/v) may be used as a developing solvent.

Figure 3:
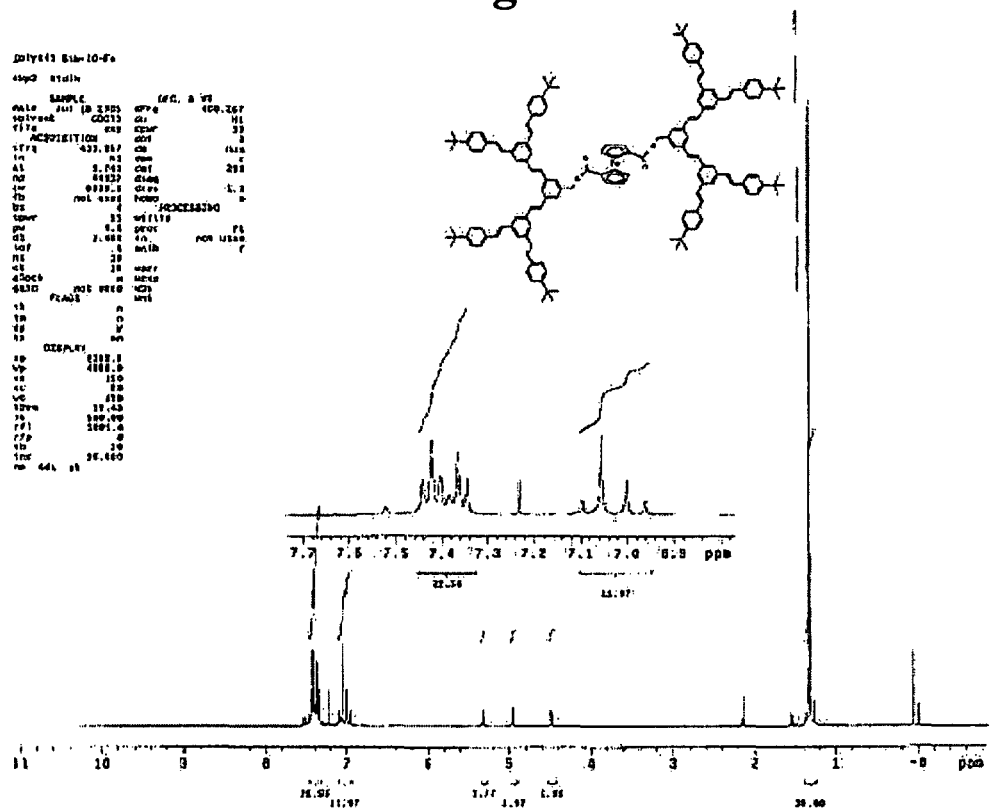
Figure 4:
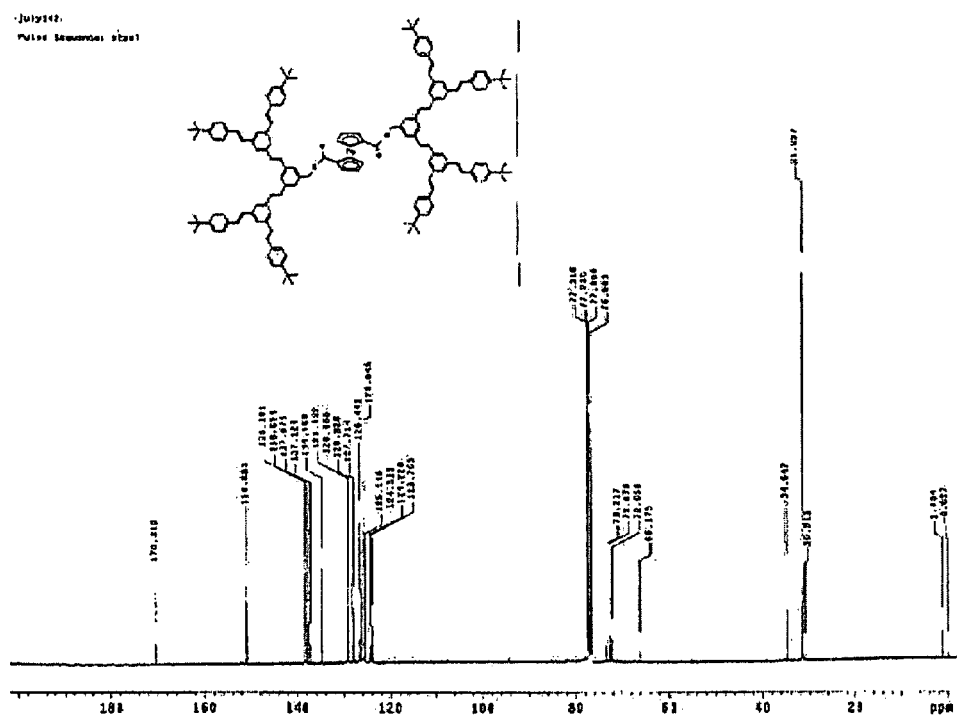
Figure 5:
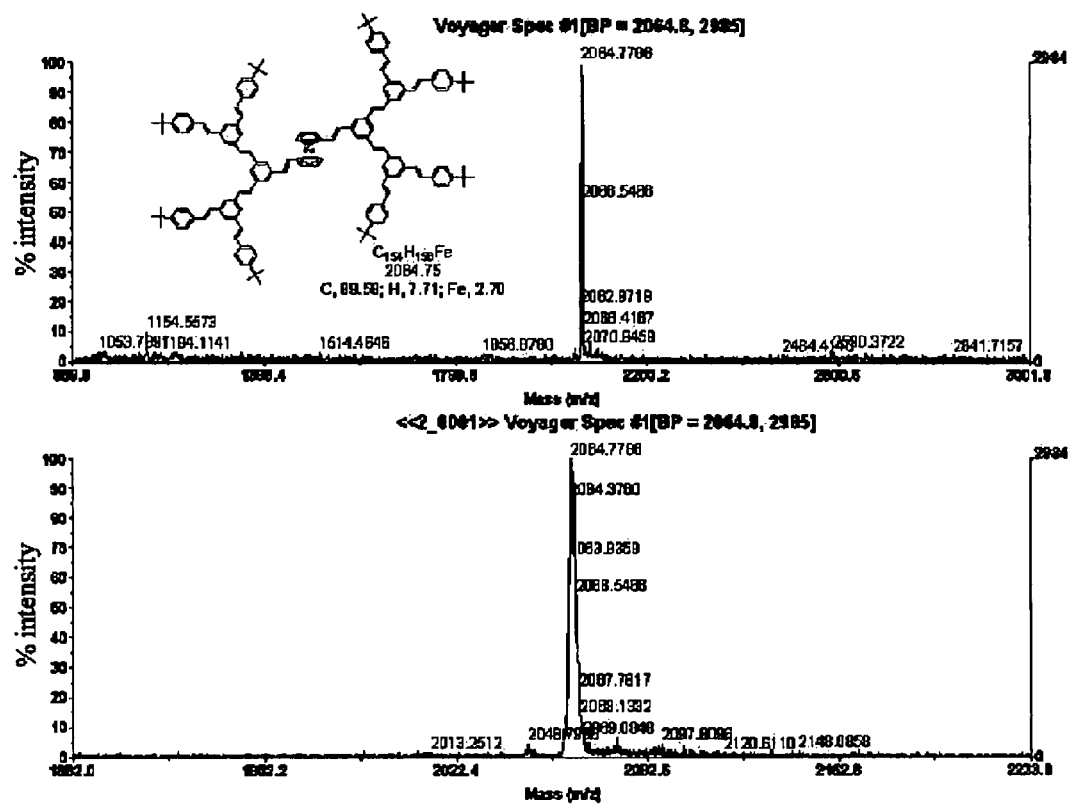

The separated STB-1GD-CHO(3,5-bis(3,5-bis(4-tert-butylstyryl)styryl)benzaldehyde) was reduced using $NaBH_4$, and thus the central aldehyde thereof was converted into a hydroxyl group, thereby synthesizing Stb-1GD-OH. This synthesized Stb-1GD-OH was dissolved in methylene chloride (MC) together with ferrocenyl-1,1-diacid fluoride and 4-dimethylamino pyridine (DMAP) and was then stirred at a temperature for about 3 hours. After the reaction was completed, the reaction mixture was diluted with methylene chloride (MC) and was then washed in water to separate an organic material layer. Then, the separated organic material layer was extracted therefrom, and adsorbed on silica gel. Subsequently, STB-1GD-FcD, represented by Formula 2, was separated from the organic material layer adsorbed on silica gel through column chromatography in which a subsidiary solvent having a volume ratio of hexane and methylene chloride of about 2:1 (v/v) may be used as a developing solvent. This separated Stb-1GD-FcD dendrimer was found and analyzed through $^1$H-NMR, $^{13}$C-NMR, and MALDI-TOF, and the results thereof was shown in FIGS. 3, 4, and 5, respectively. Further, FIG. 6 illustrates the absorbance and photoluminescence (PL) intensity of the before-synthesized Stb-1GD-OH and the separated Stb-1GD-FcD dendrimer depending on wavelength.

Figure 6:
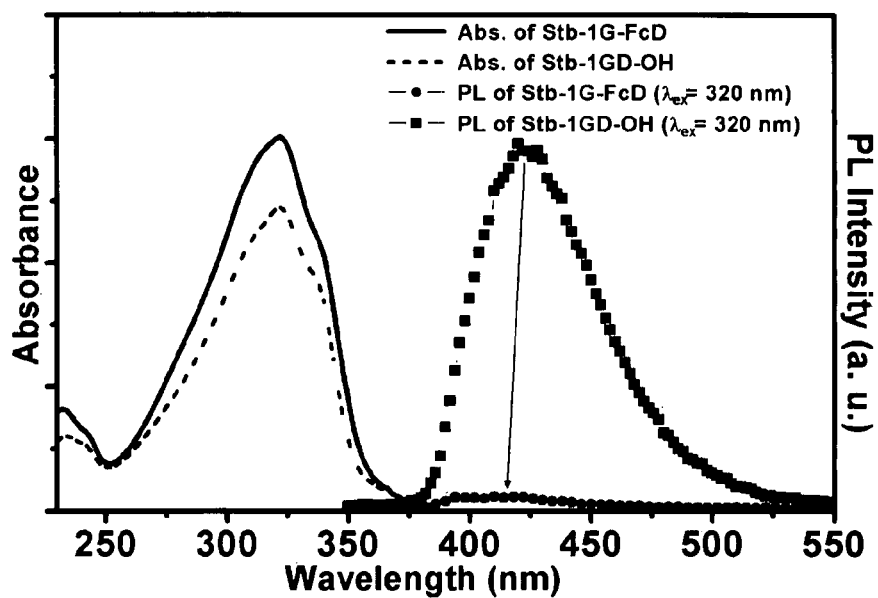

Referring to FIG. 6, the absorbance curve of the Stb-1GD-OH having no metallocene core was similar to that of the Stb-1GD-FcD dendrimer in Preparation Example 1, but the photoluminescence (PL) intensity curve of the Stb-1GD-FcD dendrimer in Preparation Example 1 was not shown. Accordingly, only the physical properties of the dendrimer, which is a material prepared in Preparation Example 1, was changed, while the chemical properties thereof were not changed. For example, the conjugated stilbene may have a property of more easily absorbing and emitting light when it is conjugated, but the dendrimer may not emit light because metallocene may be located at a core thereof, and thus, charges may be transferred. Therefore, charges may be transferred in molecules of the dendrimer.

Example 1

A glass substrate (Corning 1737) deposited with ITO was cut to a size of 0.5 mm×0.5 mm, and was then patterned using photolithography and wet etching methods. Subsequently, the substrate was dipped into acetone and isopropyl alcohol, ultrasonic-treated, and then dried. In order to form an organic active layer, about 10 mg of the Stb-1GD-FcD dendrimer obtained in Preparation Example 1 was put into about 1 ml of chlorobenzene ($C_6H_5Cl$), ultrasonic-treated for about 30 minutes and thus dissolved to obtain a mixed solution. The mixed solution passed through a syringe filter made of PTFE including pores having a size of about 0.2 μm, and the glass substrate deposited with ITO was then spin-coated thereon with the mixed solution at a speed of about 2000 rpm for about 30 seconds. The coated substrate was baked on a hot plate at a temperature of about 110° C. for about 10 minutes, and thus the remaining solvent was removed therefrom. The thickness of the organic active layer was about 50 nm~about 100 nm, and was measured using an alpha-step profilometer. This substrate was provided with a shadow mask, was put into a thermal evaporator, and then LiF was deposited to a thickness of about 5 nm on the substrate to form a barrier layer. Subsequently, aluminum (Al), which is an upper electrode, was deposited to a thickness of about 80 nm on the barrier layer through a thermal evaporation method, thereby manufacturing the organic memory device of example embodiments.

Experimental Example

Switching Characteristics Test of Memory Device

The electrical characteristics of the memory device obtained in Example 1 were evaluated using a Keithley 4200 semiconductor characteristics analysis system. The switching characteristics of the memory device manufactured in Example 1 were evaluated depending the variation of current and resistance by applying voltage to the memory device, and the results thereof were shown in FIGS. 7 and 8.

Figure 7:
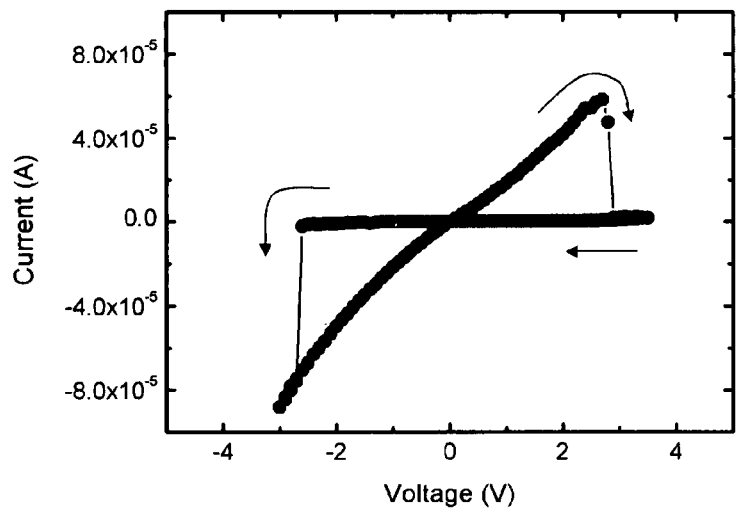
Figure 8:
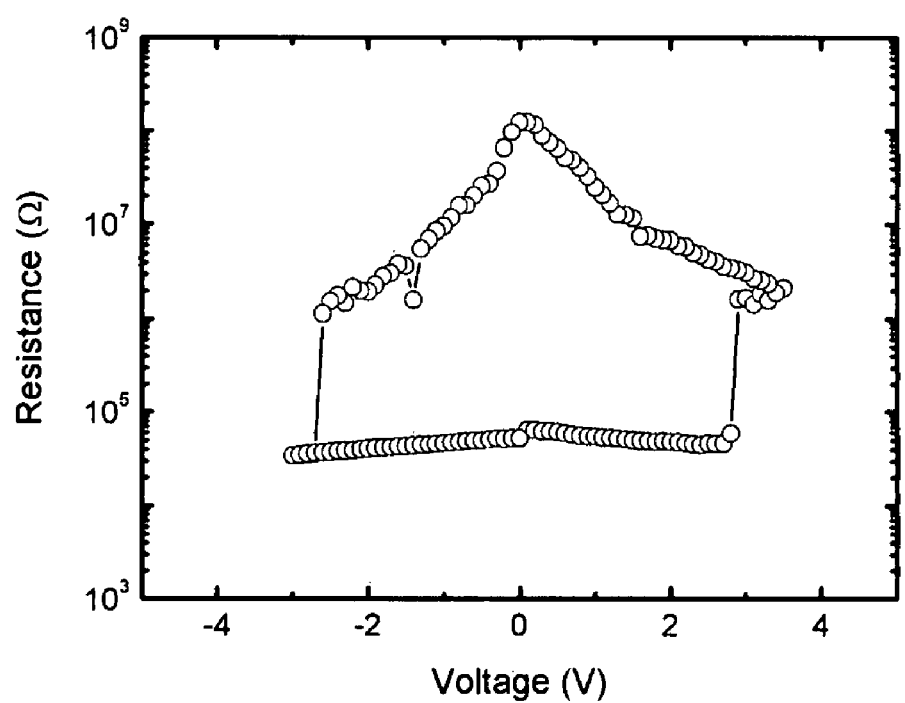

Referring to FIG. 7, two conducting states were shown in the case where the memory device was swept in two +/− directions, based on about 3V of maximum voltage. When the memory device was swept by applying plus voltage thereto, the characteristics of the memory device changed into a higher resistance state (OFF state) at about 2.6 V. In contrast, when the memory device was swept by applying minus bias voltage thereto, the characteristics of the memory device changed into a lower resistance state (ON state) at about −2.9 V. Accordingly, these two different resistance states were reversibly switched. These two different resistance states may be maintained for a relatively long time even if voltage or current was not applied. Further, as shown in FIG. 8, the variation in voltage of the memory device was shown where two-directional sweep mode voltage was continuously applied to the memory device. The two different resistance states were also maintained. As the result of measuring the resistance ratio of these two resistance states, the resistance ratio was a minimum of about $10^3$. Accordingly, it may be sufficient to be used as a memory device.

The organic memory device of example embodiments may be manufactured relatively small, and may have a shorter switching time, decreased operation voltage, decreased manufacturing cost and increased reliability, compared to an inorganic memory device, thereby realizing a light-weight highly-integrated large-capacity memory device.

Further, because the organic memory device of example embodiments may be manufactured through a relatively low-cost and simple process, e.g., a spin coating process, and may be processed at relatively low temperatures, the organic memory device may be applied to a flexible memory device.

The organic memory device manufactured using a dendrimer having a metallocene core according to example embodiments may realize improved nonvolatile memory characteristics compared to an organic memory device manufactured using a conventional conductive polymer.

As described above, although example embodiments have been disclosed for illustrative purposes, those skilled in the art will appreciate that various modifications, additions and substitutions are possible, without departing from the scope and spirit of the accompanying claims.

What is claimed is:

1. An organic memory device, comprising an organic active layer formed between a first electrode and a second electrode, wherein the organic active layer includes a dendrimer, in which metallocene is located at a core, and a conjugated dendron is connected to the core using one selected from the group consisting of an ester group of about 1 to about 20 carbon atoms, a ketone group of about 1 to about 20 carbon atoms, and an amide group of about 1 to about 20 carbon atoms as a linker.

2. The organic memory device according to claim 1, wherein the dendrimer is represented by Formula 1 below:

[Formula 1]

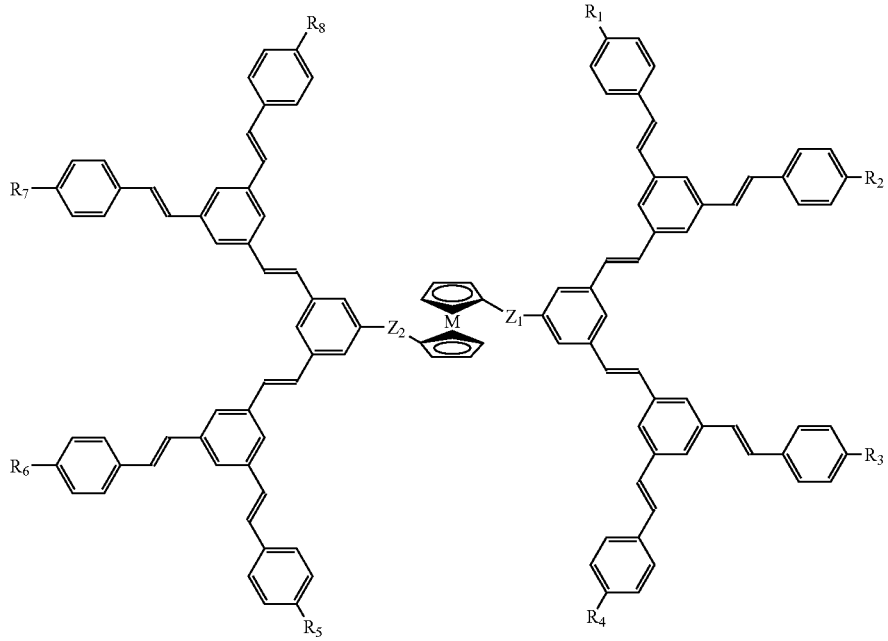

wherein, $R_1$, $R_2$, $R_3$, $R_4$, $R_5$, $R_6$ $R_7$ and $R_8$ are identical to or different from each other, and each of them is one or more independently selected from the group consisting of substituted or unsubstituted stilbene, acetylene, vinylene phenylene, fluorene, phenylene ethynylene, naphthalene, anthracene, tetracene, perylene, pyrene, thiophene, pyridine vinylene, aniline, and triphenylamine, substituted groups are identical to or different from each other, and each of them is independently selected from the group consisting of an alkyl group of $C_1$-$C_{20}$, a cycloalkyl group of $C_3$-$C_{20}$, a heterocycloalkyl group of $C_5$-$C_{30}$, an alkenyl group of $C_2$-$C_{20}$, an aryl group of $C_6$-$C_{20}$, a heteroaryl group of $C_5$-$C_{30}$, an arylalkyl group of $C_7$-$C_{20}$, and a heteroarylalkyl group of $C_7$-$C_{30}$, $Z_1$ and $Z_2$ are identical to or different from each other, and each of them is independently selected from the group of consisting of an ester group of about 1 to about 20 carbon atoms, a ketone group of about 1 to about 20 carbon atoms, and an amide group of about 1 to about 20 carbon atoms, and M is Fe, Ru, Zr or Ti.

3. The organic memory device according to claim 2, wherein the dendrimer, represented by Formula 1 above, is represented by one of Formulas 2 to 4 below

[Formula 2]
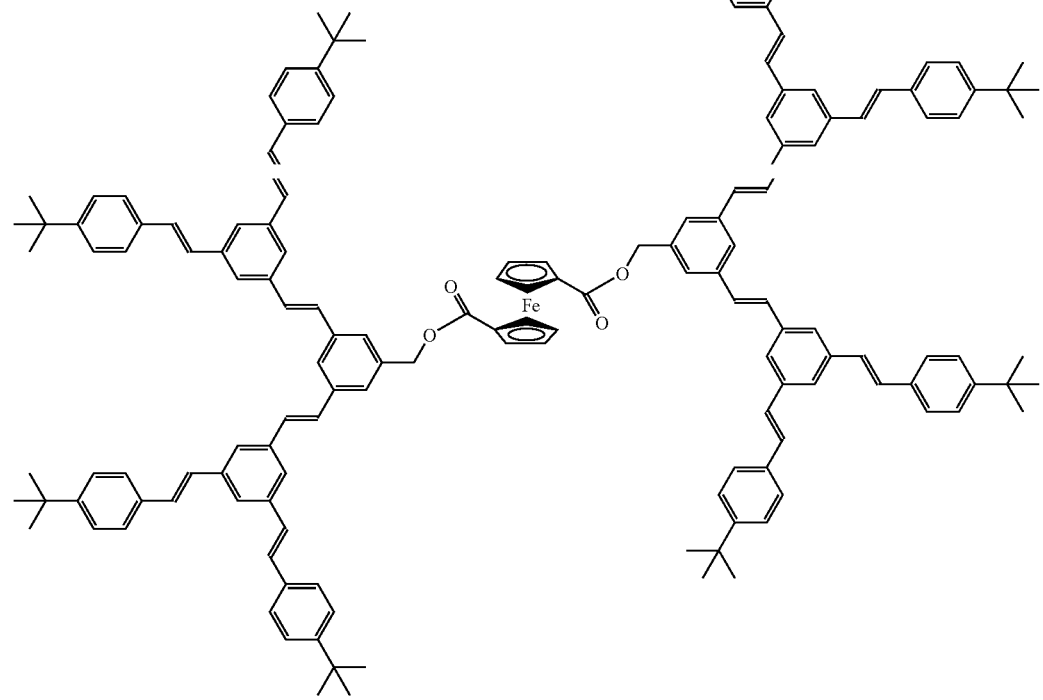
[Formula 3]
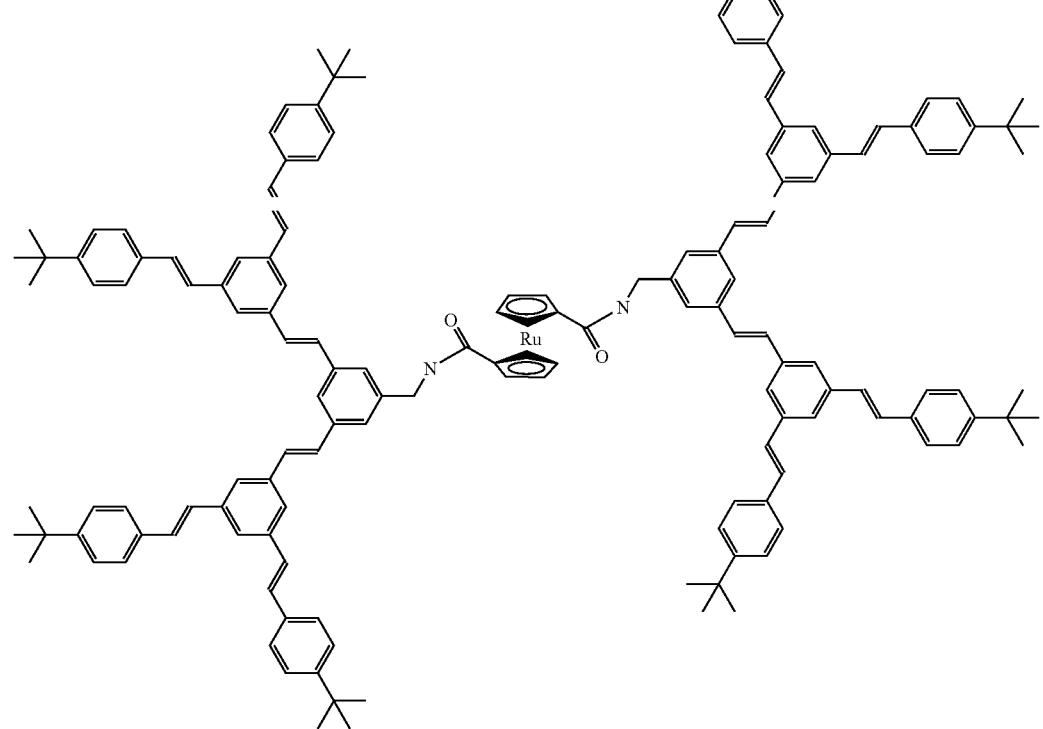

[Formula 4]

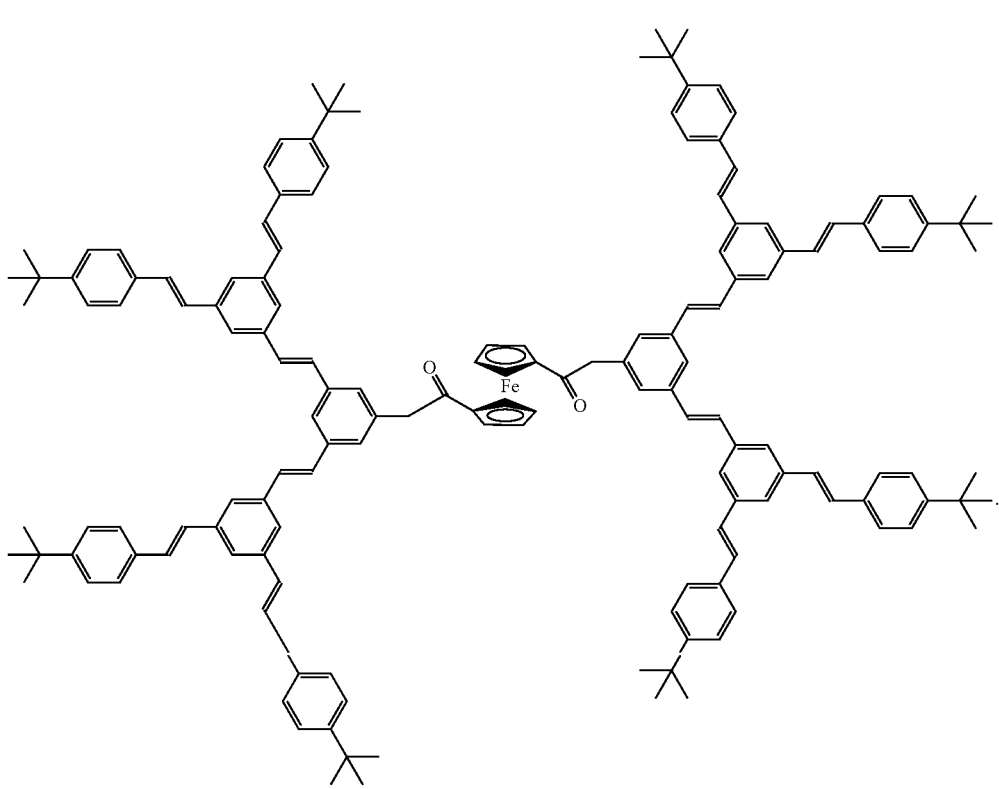

4. The organic memory device according to claim 1, wherein the first electrode or the second electrode is formed of one or more types of materials selected from the group consisting of metals, metal alloys, metal nitrides, metal oxides, metal sulfides, conductive polymers, organic conductors, nanostructures, and crystals.

5. The organic memory device according to claim 4, wherein the first electrode or the second electrode is formed of one or more selected from the group consisting of gold (Au), silver (Ag), platinum (Pt), copper (Cu), cobalt (Co), nickel (Ni), tin (Sn), titanium (Ti), tungsten (W), aluminum (Al), and indium tin oxide (ITO).

6. The organic memory device according to claim 4, wherein the conductive polymer is selected from the group consisting of polydiphenylacetylene, poly(t-butyl)diphenylacetylene, poly(trifluoromethyl)diphenylacetylene, poly(bistrifluoromethyl)acetylene, polybis(t-butyldiphenyl)acetylene, poly(trimethylsilyl)diphenylacetylene, poly(carbazole)diphenylacetylene, polydiacetylene, polyphenylacetylene, polypyridineacetylene, polymethoxyphenylacetylene, polymethylphenylacetylene, poly(t-butyl)phenylacetylene, polynitrophenylacetylene, poly(trifluoromethyl)phenylacetylene, poly(trimethylsilyl)phenylacetylene, polyaniline, polythiophene, polypyrrole, polysilane, polystyrene, polyfuran, polyindole, polyazulene, polyphenylene, polypyridine, polybipyridine, polyphthalocyanine, poly(ethylenedioxythiophene), and derivatives thereof.

7. The organic memory device according to claim 1, further comprising:

a barrier layer beneath the first electrode or on the second electrode.

8. The organic memory device according to claim 7, wherein the barrier layer includes an inorganic material selected from the group consisting of LiF, SiOx, AlOx, NbOx, TiOx, CrOx, VOx, TaOx, CuOx, MgOx, WOx and AlNOx, or an organic material selected from the group consisting of $Alq_3$, polymethylmethacrylate, polystyrene and polyethylene terephthalate (PET).

9. The organic memory device according to claim 8, wherein the barrier layer includes an inorganic material selected from the group consisting of $SiO_2$, $Al_2O_3$, $Cu_2O$, $TiO_2$, and $V_2O_3$.

10. A method of manufacturing an organic memory device, comprising forming an organic active layer between a first electrode and a second electrode, wherein the forming the organic active layer includes forming the organic active layer using a dendrimer, in which metallocene is located at a core, and a conjugated dendron is connected to the core using one selected from the group consisting of an ester group of about 1 to about 20 carbon atoms, a ketone group of about 1 to about 20 carbon atoms, and an amide group of about 1 to about 20 carbon atoms as a linker.

11. The method of manufacturing the organic memory device layer according to claim 10, wherein the dendrimer having a metallocene core is represented by Formula 1 below:

[Formula 1]

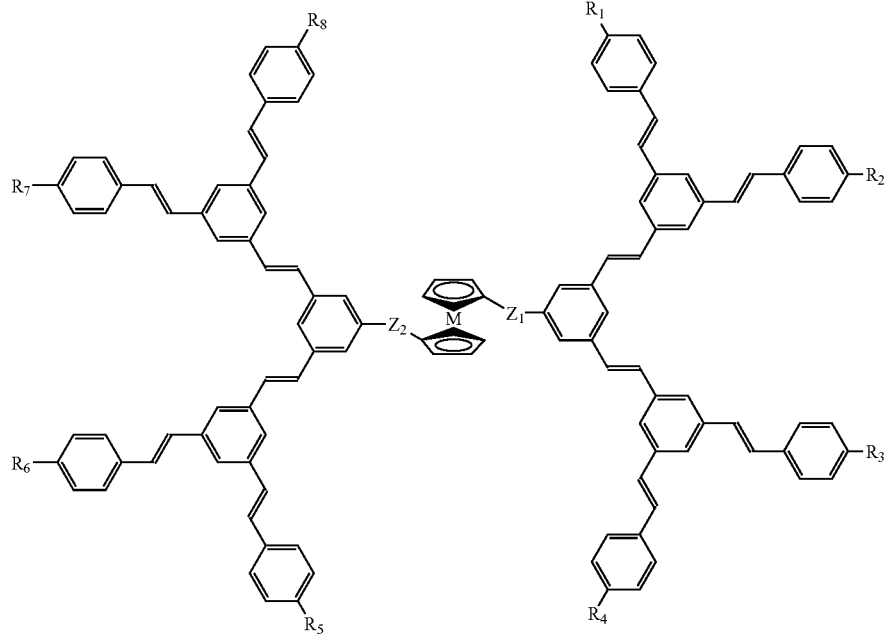

wherein, $R_1, R_2, R_3, R_4, R_5, R_6 R_7$ and $R_8$ are identical to or different from each other, and each of them is one or more independently selected from the group consisting of substituted or unsubstituted stilbene, acetylene, vinylene phenylene, fluorene, phenylene ethynylene, naphthalene, anthracene, tetracene, perylene, pyrene, thiophene, pyridine vinylene, aniline, and triphenylamine, substituted groups are identical to or different from each other, and each of them is independently selected from the group consisting of an alkyl group of $C_1$-$C_{20}$, a cycloalkyl group of $C_3$-$C_{20}$, a heterocycloalkyl group of $C_5$-$C_{30}$, an alkenyl group of $C_2$-$C_{20}$, an aryl group of $C_6$-$C_{20}$, a heteroaryl group of $C_5$-$C_{30}$, an arylalkyl group of $C_7$-$C_{20}$, and a heteroarylalkyl group of $C_7$-$C_{30}$, $Z_1$ and $Z_2$ are identical to or different from each other, and each of them is independently selected from the group consisting of an ester group of about 1 to about 20 carbon atoms, a ketone group of about 1 to about 20 carbon atoms, and an amide group of about 1 to about 20 carbon atoms, and M is Fe, Ru, Zr or Ti.

12. The method of manufacturing the organic memory device according to claim 11, wherein the dendrimer, represented by Formula 1 above, is represented by one of Formulas 2 to 4 below

[Formula 2]

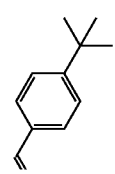

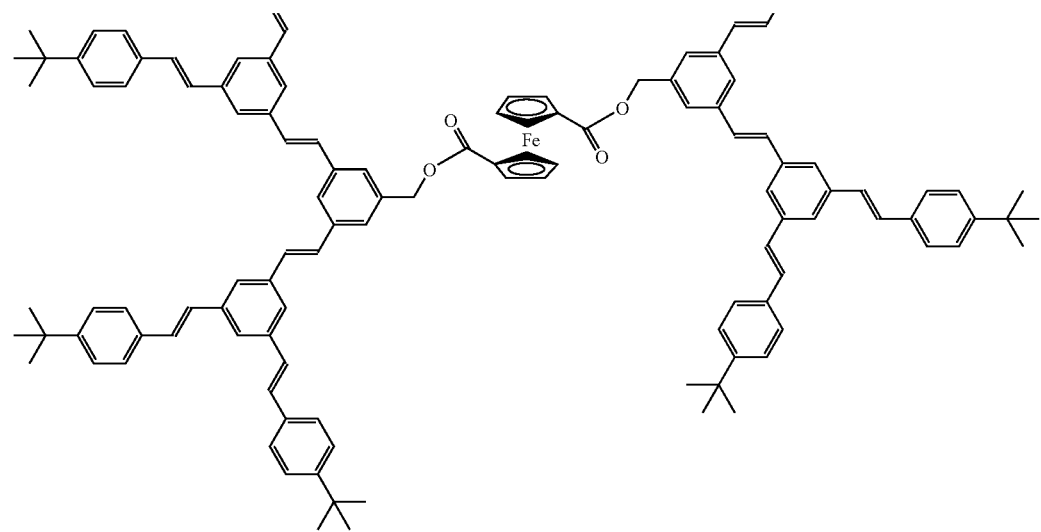
[Formula 3]
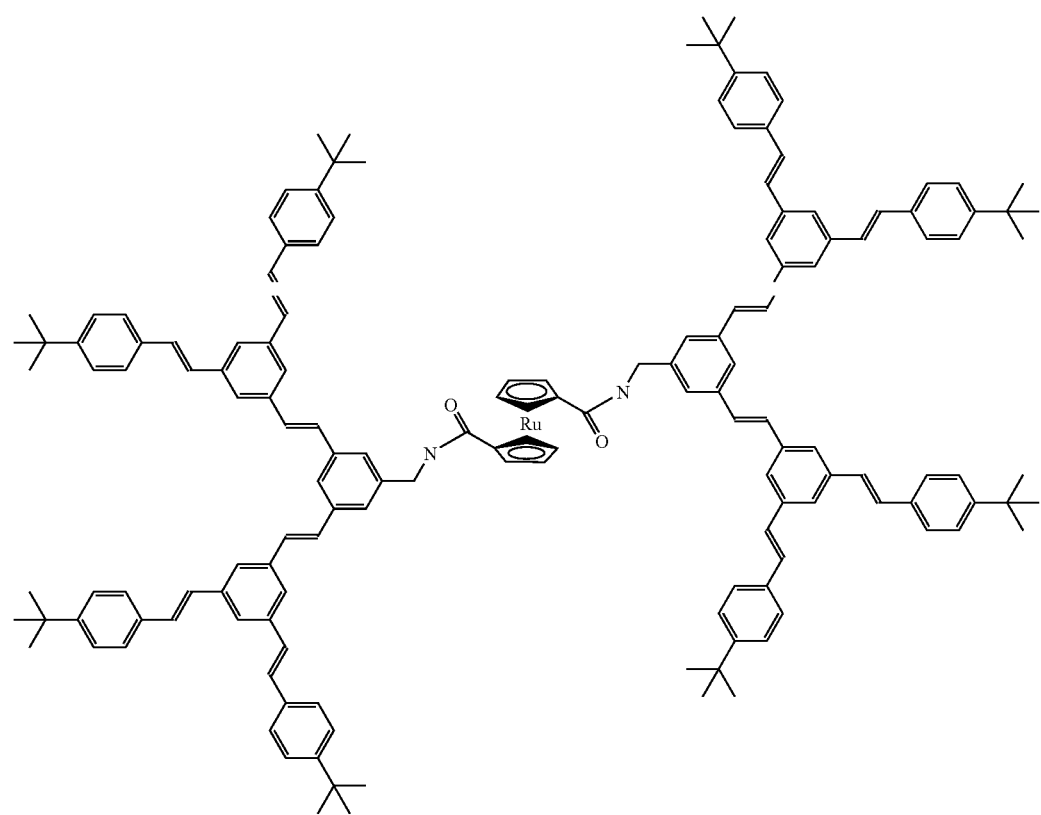

[Formula 4]

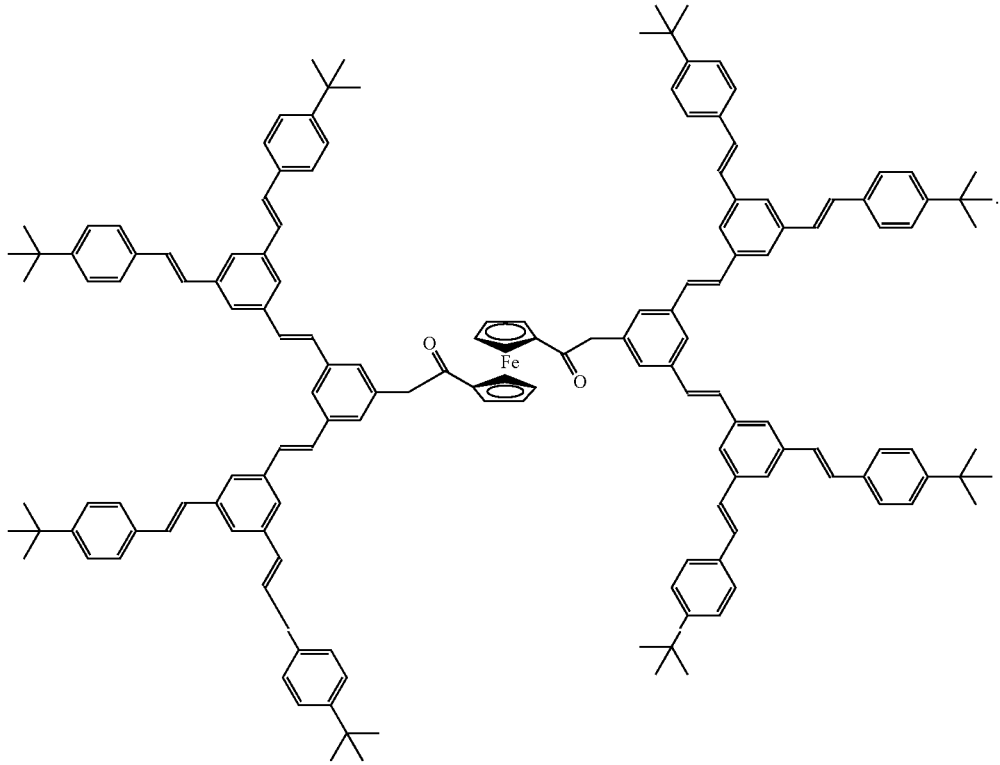

13. The method of manufacturing the organic memory device according to claim 10, wherein the forming the organic active layer further includes applying the dendrimer using one method selected from the group consisting of spin coating, spray coating, electrostatic coating, dip coating, blade coating, roll coating, and ink jet printing.

14. The method of manufacturing the organic memory device according to claim 13, wherein a solvent, used in applying the dendrimer, is one or more selected from the group consisting of chloroform, N-methylpyrrolidone, acetone, cyclopentanone, cyclohexanone, methylethylketone, ethyl cellosolve acetate, butylacetate, ethyleneglycol, toluene, xylene, tetrahydrofuran, dimethylformamide, chlorobenzene, and acetonitrile.

15. The method of manufacturing the organic memory device according to claim 10, wherein the first electrode or the second electrode is formed of one or more kinds of materials selected from the group consisting of metals, metal alloys, metal nitrides, metal oxides, metal sulfides, conductive polymers, organic conductors, nanostructures, and crystals.

16. The method of manufacturing the organic memory device according to claim 10, further comprising:
forming a barrier layer beneath the first electrode of the organic memory device or on the second electrode of the organic memory device.

* * * * *